(12) United States Patent
Ito et al.

(10) Patent No.: US 8,074,547 B2
(45) Date of Patent: Dec. 13, 2011

(54) AUTOMATIC SLICING APPARATUS

(75) Inventors: Tetsumasa Ito, Chiba (JP); Tatsuya Miyatani, Chiba (JP); Koji Fujimoto, Chiba (JP)

(73) Assignee: Seiko Instruments Inc., Chiba (JP)

( * ) Notice: Subject to any disclaimer, the term of this patent is extended or adjusted under 35 U.S.C. 154(b) by 735 days.

(21) Appl. No.: 11/657,274

(22) Filed: Jan. 24, 2007

(65) Prior Publication Data

US 2007/0180965 A1  Aug. 9, 2007

(30) Foreign Application Priority Data

Jan. 25, 2006  (JP) .................................. 2006-016156

(51) Int. Cl.
*G01N 1/31* (2006.01)
*G01N 1/06* (2006.01)
*G01N 1/04* (2006.01)

(52) U.S. Cl. ............ 83/76.8; 83/915.5; 83/167; 83/521; 83/169; 83/919

(58) Field of Classification Search ............... 83/14–15, 83/169–171, 22, 915.5, 919, 713, 714, 412, 83/42, 167, 703, 409.2, 520, 521; 62/51.1, 62/320; 73/863.11
See application file for complete search history.

(56) References Cited

U.S. PATENT DOCUMENTS

| | | | | |
|---|---|---|---|---|
| 3,103,844 A | * | 9/1963 | Persson | 83/167 |
| 3,771,405 A | | 11/1973 | Blum | |
| 3,832,923 A | * | 9/1974 | Lassmann et al. | 83/16 |
| 4,377,958 A | * | 3/1983 | Leighton | 83/410.7 |
| 5,713,255 A | * | 2/1998 | Izvozichikov et al. | 83/24 |
| 6,387,653 B1 | * | 5/2002 | Voneiff et al. | 435/40.52 |
| 2005/0179892 A1 | * | 8/2005 | Gerstner et al. | 356/318 |
| 2005/0235542 A1 | * | 10/2005 | Metzner et al. | 42/24 |
| 2007/0204740 A1 | * | 9/2007 | Miyatani et al. | 83/919 |

FOREIGN PATENT DOCUMENTS

| | | |
|---|---|---|
| EP | 305123 A1 | 3/1989 |
| JP | 2001-338277 A | 12/2001 |
| JP | 2004-28910 | 1/2004 |
| WO | WO 98/02851 A1 | 1/1998 |

OTHER PUBLICATIONS

European Search Report for European Application No. 07250216, dated Sep. 24, 2009, 1 page.

* cited by examiner

*Primary Examiner* — Laura M. Lee
(74) *Attorney, Agent, or Firm* — Brinks Hofer Gilson & Lione (57) ABSTRACT

An automatic slicing apparatus reduces the likelihood of failure to make a sliced piece specimen even if continuously operated. The apparatus, on the basis of an exchange command signal, detaches a sample block attached to a cutting base and attaches a new sample block to the cutting base. The apparatus cuts a sliced piece of a predetermined thickness by moving a knife with respect to the sample block having been attached to the cutting base. The apparatus also observes the sliced piece having been cut and judges the sliced piece by comparing an observation data obtained by the observation means and a sample block cut face data. When the apparatus judges that the sliced piece is good, the apparatus transmits an exchange command signal.

6 Claims, 8 Drawing Sheets

AUTOMATIC SLICING APPARATUS

This application claims priority under 35 U.S.C. §119 to Japanese Patent Application Nos. JP2006-016156 filed Jan. 25, 2006, the entire content of which is hereby incorporated by reference.

BACKGROUND OF THE INVENTION

1. Field of the Invention

The present invention relates to an automatic slicing apparatus and an automatic slicing method, each of which is used when making a sliced piece specimen used in a physicochemical experiment, a microscope observation and the like.

2. Description of the Related Art

The sliced piece specimen used in the physicochemical experiment and the microscope observation is one in which a sliced piece whose thickness is several μm (e.g., 3 μm-5 μm) has been fixed onto a base plate such as slide glass. Generally, the sliced piece specimen is made by utilizing a microtome. Here, there is explained about a method of making the sliced piece specimen, which has utilized the microtome.

First, after an organism sample, such as creature and animal which have been formalin-fixed, has been paraffin-substituted, additionally its periphery is solidified by the paraffin, thereby making an embedded block under a block state. Next, this embedded block is set to the microtome that is a slicing apparatus for exclusive use, thereby performing a rough cutting. By this rough cutting, a surface of the embedded block is smoothened, and the embedded organism sample that is an object article of the experiment and the observation is exposed to the surface.

After this rough cutting has finished, a main cutting is performed. This is a process of very thinly slicing the embedded block in the above-mentioned thickness by a cutting blade that the microtome has. By this, it is possible to obtain a sliced piece.

Subsequently, there shifts to an extension process extending the sliced piece having been obtained by the main cutting. In other words, since the sliced piece having been made by the main cutting is one having been sliced in the very thin thickness as having been mentioned above, it becomes a wrinkled state or a rounded state (e.g., like a letter of U). Thereupon, it is necessary to extend the sliced piece by removing the wrinkle or the roundness by the extension process.

Generally, it is extended by utilizing water and hot water. In the beginning, the sliced piece having been obtained by the main cutting is immersed in the water. By this, the large wrinkle or roundness of the sliced piece is removed while preventing a mutual adhesion of the paraffin embedding the organism sample. Thereafter, the sliced piece is immersed in the hot water. By this, since the sliced piece becomes liable to extend, it is possible to remove the remaining wrinkle or roundness, which could not be removed completely by the immersion in the water.

And, the sliced piece having finished the extension by the hot water is scooped up by the base plate such as slide glass, and mounted onto the base plate. Incidentally, at this point of time, in a case where if the extension has been insufficient, a heat is exerted on the sliced piece by being mounted together with the base plate onto a hot plate and the like. By this, it is possible to more extend the sliced piece.

Finally, the base plate on which there has been mounted the sliced piece is put into a drier and dried. By this drying, a moisture having adhered by the extension evaporates, and the sliced piece is fixed onto the base plate. As a result, it is possible to make the sliced piece specimen.

The sliced piece specimen having been made like this is used in the fields of biology and medicine, and the like.

Besides a method of diagnosing a normality/abnormality of tissue from a shape of cell, which has been performed from olden times, in recent years by a development in genome science, there increases a need comprehensively and histologically seeing a manifestation of gene or protein. For this reason, there has become arisen a necessity for efficiently making increasingly more sliced piece specimens. However, since most of the conventional processes having been mentioned above are ones requiring high techniques and experiences, they can be dealt with only by a manual work of skilled worker, so that they have been ones requiring time and effort.

Thereupon, in order to solve the defect like this even a little, there is provided a slicing apparatus automatically performing the rough cutting process and the main cutting process, which are one portions of the above-mentioned processes (for example, JP-A-2004-28910).

This apparatus automatically performs a process of making a sliced piece by cutting an embedded block having been set, a process of carrying the sliced piece, which has been made, by a carrier tape to thereby transcribe it onto a slide glass, and a process of carrying the sliced piece together with the slide glass till an extension device to thereby perform an extension.

According to this apparatus, it is possible to reduce a load of the worker, and an artificial mistake by the worker can be made null as well, so that it is possible to make a good sliced piece specimen.

However, in the above apparatus described in JP-A-2004-28910, the following problems have been left.

That is, although the above-mentioned apparatus is an apparatus which can automatically make the sliced piece from the embedded block having been previously set, and can fix the sliced piece onto the slide glass under a state in which its extension has been finished, when operating the apparatus there are changes in conditions, which cannot be predicted, such as a situation of pretreatment with respect to the organism sample, a kind of the organism sample and a difference in cutting direction, so that it has been very difficult to perform the cutting, an extension processing after that, and the like under constant conditions. For this reason, a probability of failure in making the sliced piece specimen is high and, notwithstanding the facts that it is an automated apparatus, it has been impossible to continuously operate the apparatus.

SUMMARY OF THE INVENTION

The present invention has been made in view of the circumstances like this, and its object is to provide an automatic slicing apparatus and an automatic slicing method, each of which can continuously cut a sliced piece from plural sample blocks with a less fear of failing to make the sliced piece specimen even if continuously operated and, moreover, without causing a hand to intervene.

In order to solve the above problems, the present invention has adopted the following constitutions.

That is, an automatic slicing apparatus concerned with the present invention is characterized by having possessed a sample block attaching/detaching means which, on the basis of an exchange command signal, detaches a sample block attached to a cutting base and instead attaches a new sample block to the cutting base, a cutting means which cuts a sliced piece of a predetermined thickness by relatively moving a knife with respect to the sample block having been attached to the cutting base, an observation means observing the sliced piece having been cut, and an evaluation means which judges whether the sliced piece is good or not good by an observation data having been obtained by the observation means and which, when there has been judged that the sliced piece is good, transmits an exchange command signal to the effect that the sample block is to be exchanged to the sample block attaching/detaching means.

According to the present invention, with respect to the sliced piece having been cut, the judgment on whether it is good or not good is extemporaneously performed by the evaluation means and, in a case where there has been judged good, there is exchanged to the new sample block by the sample block attaching/detaching means to thereby cut the sliced piece from this new sample block and, in a case where there has been judged not good, the sliced piece is cut again from the sample block attached to the cutting base. In other words, only in the case where there has been judged good by the valuation means, the sample block is exchanged and, in the case not good, the sliced piece is cut again from the same sample block, so that the fear of failing to make the sliced piece specimen is very small even if continuously operated.

An automatic slicing apparatus concerned with the present invention is characterized in that the observation data is a picture data having been obtained by taking, by an epi-illumination, an image of the sliced piece having been disposed on a surface of a mirror-reflecting medium, together with the medium around the sliced piece.

According to the present invention, in a case where the light by the epi-illumination is applied to the sliced piece, since it is scattered, its reflected light becomes weak. On the other hand, when the light has been applied to the medium around the sliced piece, since it is regularly reflected, the reflected light becomes strong. As a result, by a difference in luminance, it is possible to grasp an external shape of the sliced piece and an existence of inside hole.

An automatic slicing apparatus concerned with the present invention is characterized in that the observation data is a picture data having been obtained by taking, by a transmission illumination, an image of the sliced piece having been disposed in a transparent medium, together with the transparent medium around the sliced piece.

According to the present invention, in a case where the light by the transmission illumination passes through the sliced piece, since the light is absorbed and scattered by the sliced piece, the transmission light becomes weak. On the other hand, when the light passes through the transparent medium around the sliced piece, since the light passes almost intact, the transmission light becomes strong. As a result, by the difference in luminance, it is possible to grasp the external shape of the sliced piece and the existence of inside hole.

An automatic slicing apparatus concerned with the present invention is characterized in that the evaluation means judges whether the sliced piece is good or not good by a light-dark data having been obtained by binarization-processing the picture data on the basis of a luminance information.

According to the present invention, by binarization-processing the picture data of the sliced piece, it is possible to darkly indicate a sliced piece portion, and brightly an outside of the sliced piece. By this, it is possible to more clearly grasp the external shape and the like of the sliced piece.

An automatic slicing apparatus concerned with the present invention is characterized in that the evaluation means judges whether the sliced piece is good or not good by comparing the observation data having been obtained by the observation means and a sample block cut face data having been previously inputted and, when there has been judged that the sliced piece is good, transmits the exchange command signal to the effect that the sample block is to be exchanged to the sample block attaching/detaching means.

According to the present invention, since there is judged whether the sliced piece is good or not good by comparing the observation data having been obtained by the observation means and the sample block cut face data having been previously inputted, the judgment on whether it is good or not good can be easily performed for the fact that there exists the sample block cut face data which becomes a reference for the judgement on whether it is good or not good.

An automatic slicing apparatus concerned with the present invention is characterized in that the evaluation means judges whether the sliced piece is good or not good by comparing a light-dark data having been obtained by binarization-processing the picture data on the basis of a luminance information and the sample block cut face data.

According to the present invention, from the facts that, by binarization-processing the picture data of the sliced piece, it is possible to darkly indicate the sliced piece portion, and brightly the outside of the sliced piece, and that there exists one becoming the reference for the judgment on whether it is good or not good, the judgment on whether the sliced piece is good or not good can be easily performed.

An automatic slicing apparatus concerned with the present invention is characterized in that, in the evaluation means, when comparing the light-dark data and the sample block cut face data, a virtual sliced piece picture obtained from the light-dark data and a sample block cut face picture obtained from the sample block cut face data are compared with at least one element among an area element, a position element of barycenter, and a pattern matching element.

According to this invention, since the virtual sliced piece picture and the sample block cut face picture are compared with at least one element among the area element, the position element of barycenter, and the pattern matching element, it is possible to quantitatively denote a difference between the sample block cut face picture and the virtual sliced piece picture, so that the judgment on whether the sliced piece is good or not good can be more easily performed.

An automatic slicing method concerned with the present invention possesses a sample block attaching/detaching process which detaches a sample block attached to a cutting base and instead attaches a new sample block to the cutting base, a cutting process which cuts a sliced piece of a predetermined thickness by relatively moving a knife with respect to the sample block having been attached to the cutting base, an observation process observing the sliced piece having been cut, and an evaluation process which judges whether the sliced piece is good or not good by comparing an observation data having been obtained in the observation process and a sample block cut face data having been previously inputted, and is characterized in that, in a case where there has been judged good in the evaluation process, after having shifted to the sample block attaching/detaching process, there shifts to the cutting process, the observation process and the evaluation process in order, and, in a case where there has been judged not good in the evaluation process, without shifting to the sample block attaching/detaching process, there shifts again to the cutting process, the observation process and evaluation process in order.

According to the present invention, since the sample block is exchanged only in the case where there has been judged good by the evaluation means and the sliced piece is cut again from the same sample block in the case not good, the fear of failing to make the sliced piece specimen is very small even if continuously operated.

According to this invention, the sliced piece can be continuously cut from plural sample blocks with the fear failing in making the sliced piece specimen being small even if continuously operated and, moreover, without causing the hand to intervene.

DETAILED DESCRIPTION OF THE PREFERRED EMBODIMENTS

Hereunder, there is explained about an embodiment of the present invention while referring the drawings.

Figure 1:
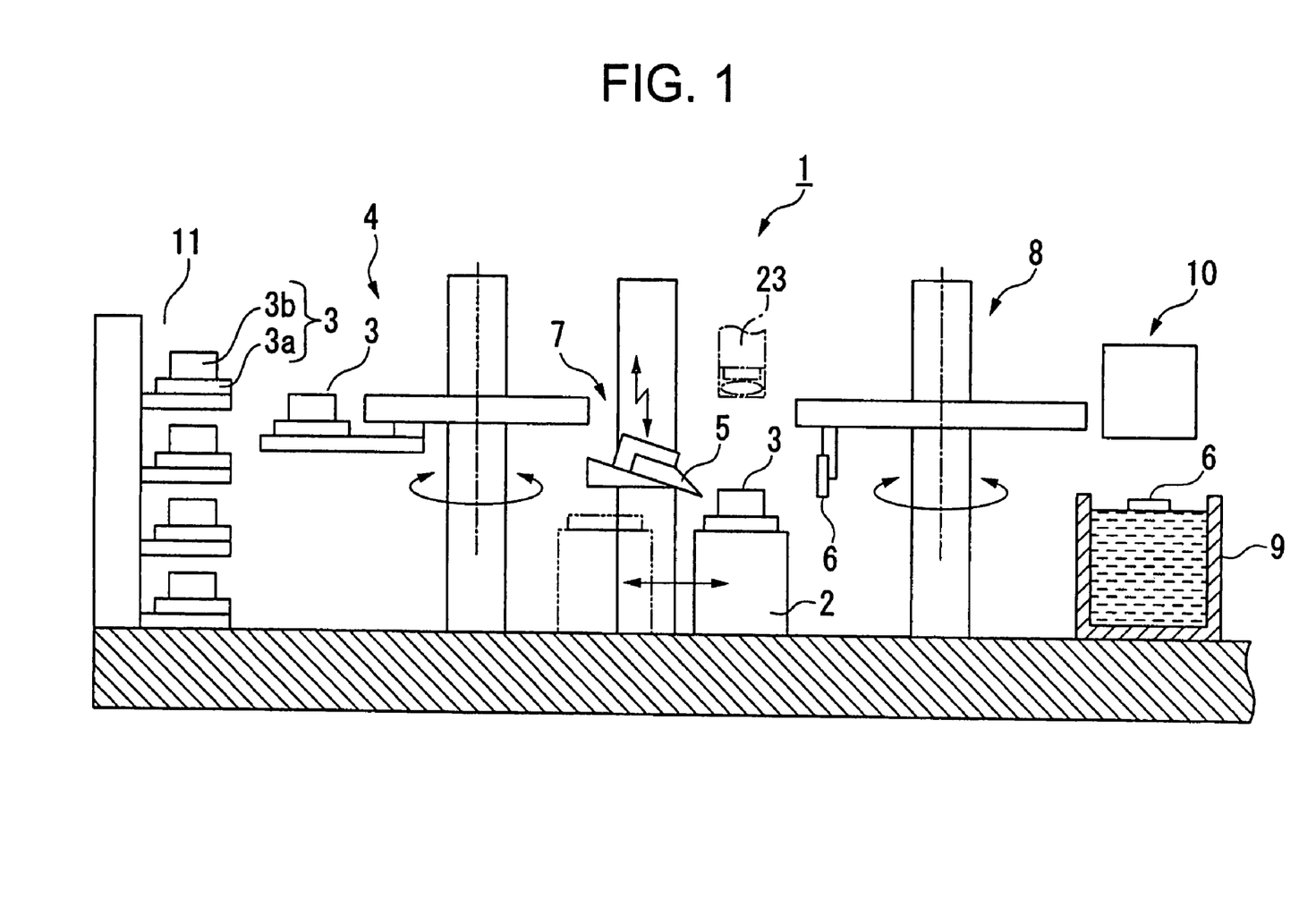
FIG. 1 is a view showing a whole constitution of an automatic slicing apparatus of an embodiment of the present invention.
Figure 2:
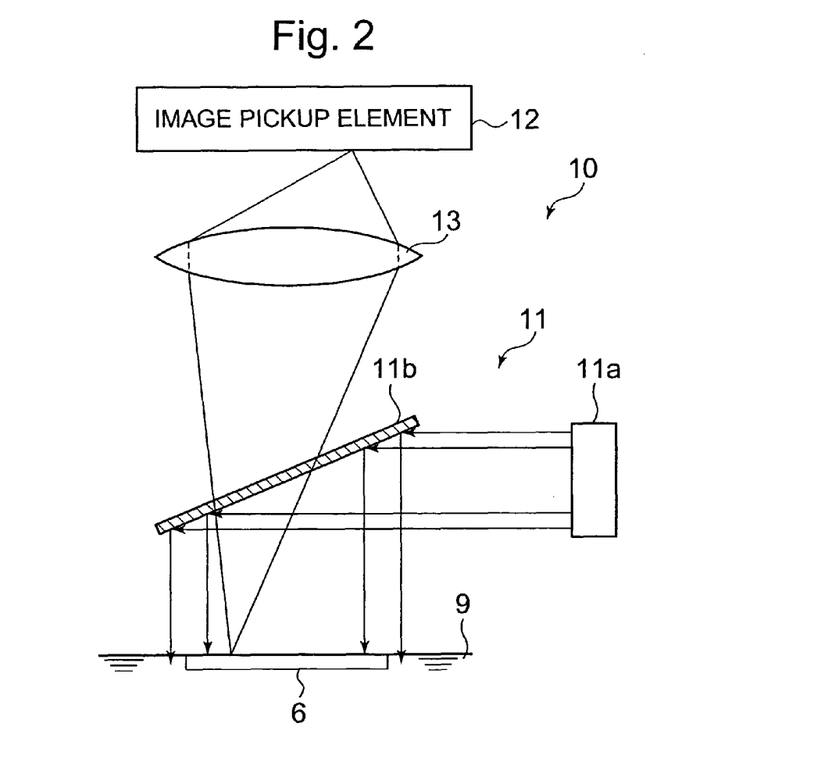
FIG. 2 is a side view explaining an observation means of the embodiment of the present invention.
Figure 3:
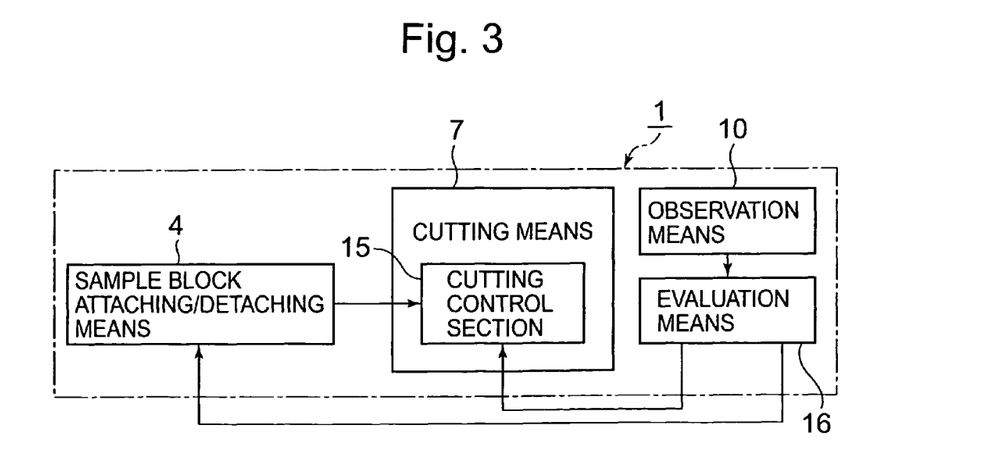
FIG. 3 is a function block diagram of a control system in the automatic slicing apparatus of the embodiment of the present invention.

FIG. 1 is a view showing a constitution of an automatic slicing apparatus, FIG. 2 a view showing an observation means, and FIG. 3 a function block diagram of a control system in the automatic slicing apparatus. An automatic slicing apparatus 1 possesses a sample block attaching/detaching means 4 comprising a block handling robot, which, on the basis of an exchange command signal, detaches a sample block 3 attached to a cutting base 2 and instead attaches the new sample block 3 to the cutting base 2, a cutting means 7 which relatively moves a knife 5 with respect to the sample block 3 having been attached to the cutting base 2 to thereby cut a sliced piece 6 of a predetermined thickness, a carrier means 8 carrying the sliced piece 6 having been cut by the cutting means 7, and an observation means 10 observing the sliced piece 6 having been carried till a water tank 9 through the carrier means 8. Incidentally, although plural sample blocks 3 are previously stored in a block keeping storehouse 11, the block sample 3 is made with an embedding block 3b being fixed onto an embedding cassette 3a.

The sample block attaching/detaching means 4 is one which selects in order the necessary sample block 3 from the plural sample blocks 3 having been stored in the block keeping storehouse 11 on the basis of a command signal from a control section not shown in the drawing, and which supplies it to the cutting base 2 of the cutting means 7 in a later stage and, at the same time, returns the sample block 3, from which the sliced piece 6 has been taken out, to a predetermined position in the block keeping storehouse 11.

The cutting means 7 possesses the cutting base 2 and the knife 5. The cutting base 2 is adapted so as to be movable along a rail not shown in the drawing between a block reception position (A) receiving the sample block from the sample block attaching/detaching means 4 and a cutoff finish position (B) cutting the sample block 3 having been attached to an upper part by the knife 5. Incidentally, FIG. 1 shows a state in which the cutting base 2 has reached to the cutoff finish position (B). Further, a sample block fixing face of the cutting base 2 is made variable in its slant around X-Y axes intersecting perpendicularly to each other on a horizontal plane and, by this, there is adapted such that a desired cutting face is obtained by slanting the sample block 3 in an arbitrary direction. Further, the knife 5 is made such that its height can be adjusted by a vertically moving mechanism and, by this, there is made such that a cutting thickness of the sliced piece 6 can be arbitrarily set.

The carrier means 8 is one carrying the sliced piece 6, which has been cut by the cutting means 7, such that it is immersed in the water tank 9, and there are utilized, e.g., one carrying the sliced piece 6 by suction-adhering it by utilizing a negative pressure to a tip of a rotary arm having been rotatably supported by a supporting post, one carrying the sliced piece 6 by a belt possessing an adhesion part adhering it by utilizing an adhesive or a static electricity, and the like.

As shown in FIG. 2, the observation means 10 possesses an epi-illumination system 14 applying a collimate light parallel to a normal of a surface of a surface-reflecting medium (e.g., water) C, an image pickup element 12, such as CCD, which takes an image of the sliced piece 6 together with the medium C around it, and an image formation lens 13 having an optical axis parallel to the normal of the surface of the medium C and forming an image of a reflected light from the sliced piece 6 and its peripheral medium on the image pickup element 12. The epi-illumination system 14 comprises a face light emission source 14a making a parallel light, and a half mirror 14b which reflects the parallel light having been irradiated from the face light emission source 14a to the sliced piece 6 side, and through which the reflected light from the sliced piece 6 and its peripheral medium permeates.

Incidentally, as a light source, besides the face light emission source 14a, it may be one which causes the light from a point light source to pass through a pinhole and a collimator lens, thereby changing it to the parallel light. Further, positions of the face light emission source 14a and the half mirror 14b are set such that the parallel light having been bent to the sliced piece 6 side by the half mirror 14b goes perpendicularly to the surface of the medium C.

In explaining about a control system of the automatic slicing apparatus, as shown in FIG. 3, in the cutting means 7 there is provided a cutting control section 15 which controls a relative velocity (cutting velocity) between the embedding block 3b on the embedding cassette 3a and a blade cutting the embedding block 3b, and controls a feed quantity of the blade. A control part of the sample block attaching/detaching means 4 and an evaluation means 16 are electrically connected respectively to the cutting control section 15. The evaluation means 16 is electrically connected respectively to the observation means 10 and the control part of the sample block attaching/detaching means 4.

The evaluation means 16 is one which judges whether the sliced piece 6 is good or not good by comparing an observation data having been obtained by the observation means 10 and a sample block cut face data having been previously inputted and, when having judged that the sliced piece is good, transmits the exchange command signal to the effect that the sample block is exchanged to the sample block attaching/detaching means 4.

Figure 4:
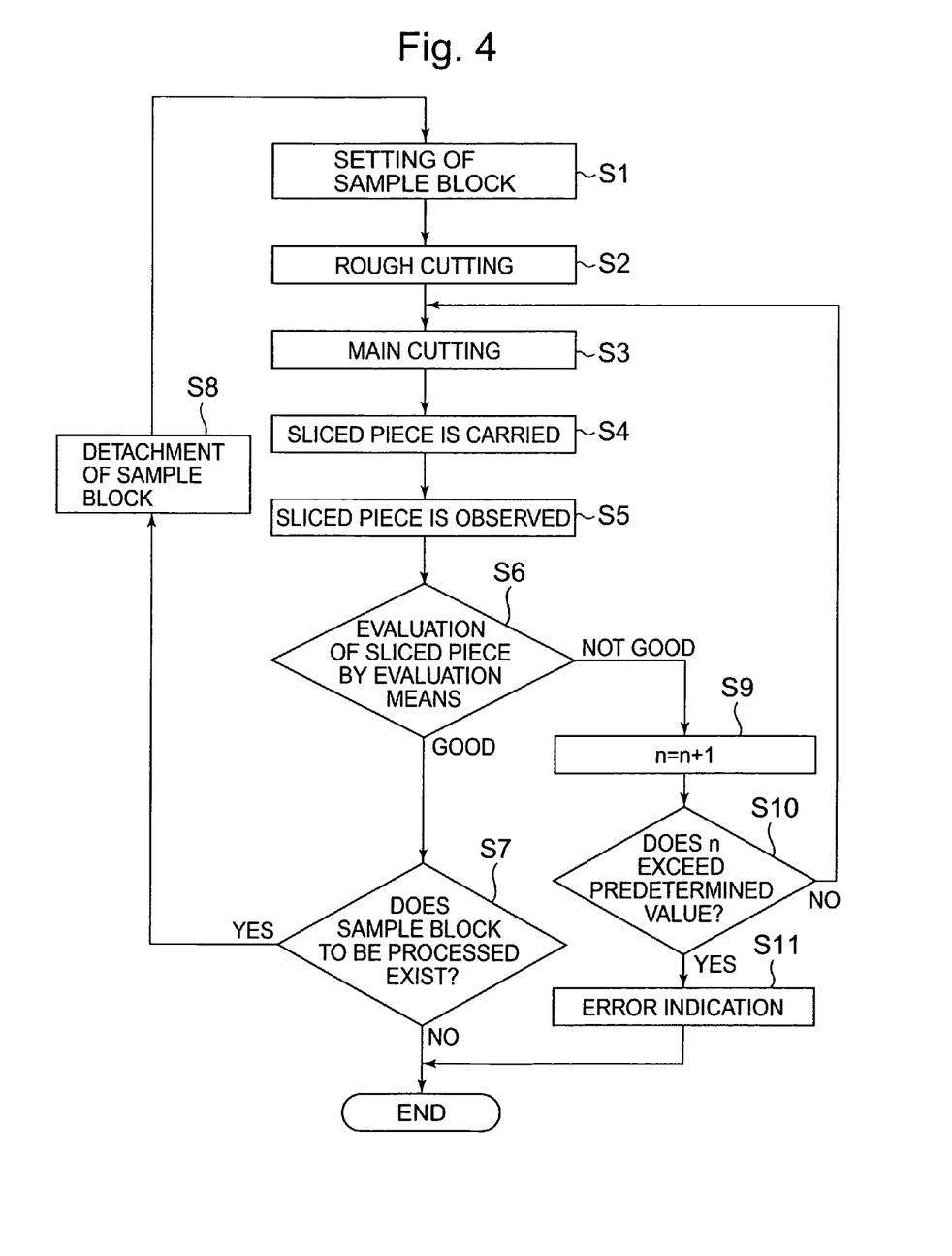
FIG. 4 is a flowchart explaining an automatic slicing method having used the automatic slicing apparatus of the embodiment of the present invention.

Next, there is explained about an automatic slicing method having used the automatic slicing apparatus of the above constitution while referring to a flowchart shown in FIG. 4. Incidentally, the following processings are all automatically performed by a computer without through a hand.

First, the sample block 3 is set onto the cutting base 2 by the sample block attaching/detaching means 4 (step S1). If the setting is completed, an information to that effect is outputted in the form of signal from the control part of the sample block attaching/detaching means 4 to the cutting control section 15 of the cutting means 7, the rough cutting by the cutting means 7 is started, the surface of the embedding block 3b is made a smooth face, and the embedded organism sample that is the object article of the experiment or the observation is exposed to the surface (step S2). And, there shifts to the main cutting, and a cut surface of the embedding block 3b is very thinly sliced in a predetermined thickness by the knife 5 whose height has been adjusted (step S3).

Figure 5:
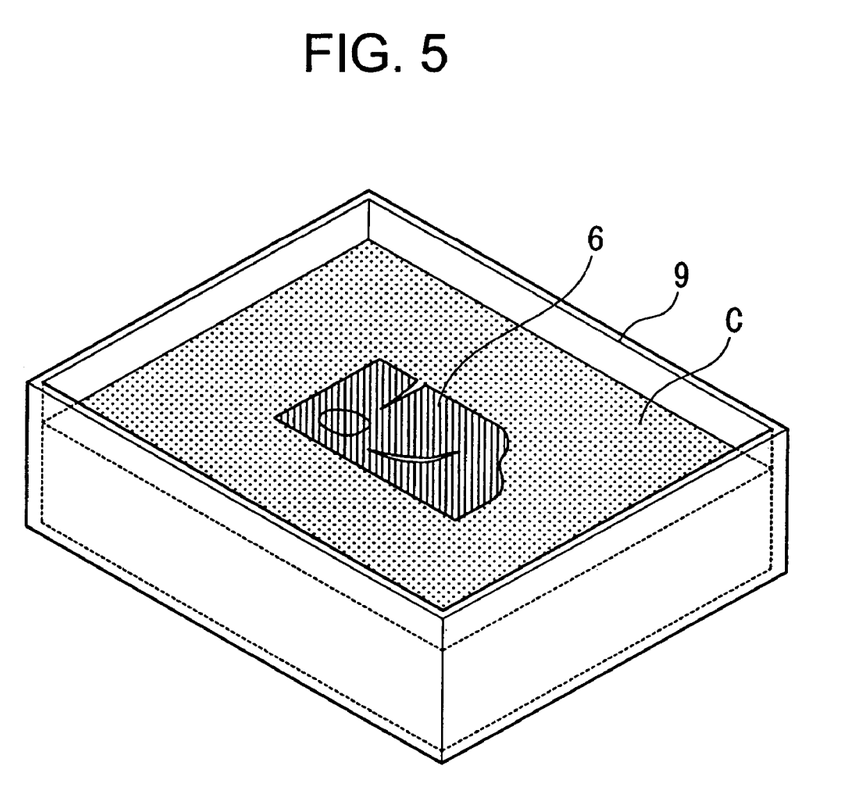
FIG. 5 is a perspective view explaining a sliced piece having been cut by the automatic slicing apparatus of the embodiment of the present invention.

Thereafter, the sliced piece 6 having been obtained is carried to the water tank 9 by the carrier means 8 and, when the sliced piece 6 has been extended as shown in FIG. 5, the sliced piece 6 is observed (steps S4, S5). That is, an image of the sliced piece 6 having floated on a water surface is taken together with the water in its periphery by the image pickup element 12 by an epi-illumination of the observation means 10.

At this time, in a case where the light by the epi-illumination is applied to the sliced piece 6, since the light is scattered or absorbed because some irregularities exist in the sliced piece surface, the reflected light from there becomes weak. On the other hand, when the light has been applied to the medium (in FIG. 5, the water surface) in the periphery of the sliced piece 6, since it is regularly reflected, the reflected light becomes strong. For this reason, as shown in FIG. 6A, there is obtained a picture in which a place where the sliced piece 6 exists is darkly displayed in comparison with the periphery.

Incidentally, in this picture, a sign Za denotes a water surface portion, Zb a sliced piece portion, Zba an organism sample portion in the sliced piece, Zbb a broken portion in the sliced piece, and Zbc a portion in which the sliced piece has lacked, respectively.

The picture having been obtained is sent to the evaluation means 16 in the form of picture data. In the evaluation means 16, the picture data having been sent from the observation means 10 is binarization-processed on the basis of a luminance information, a light-dark data having been obtained is compared with the sample block cut face data, and there is judged whether the sliced piece 6 having been cut is good or not good (step S6).

Figure 6A:
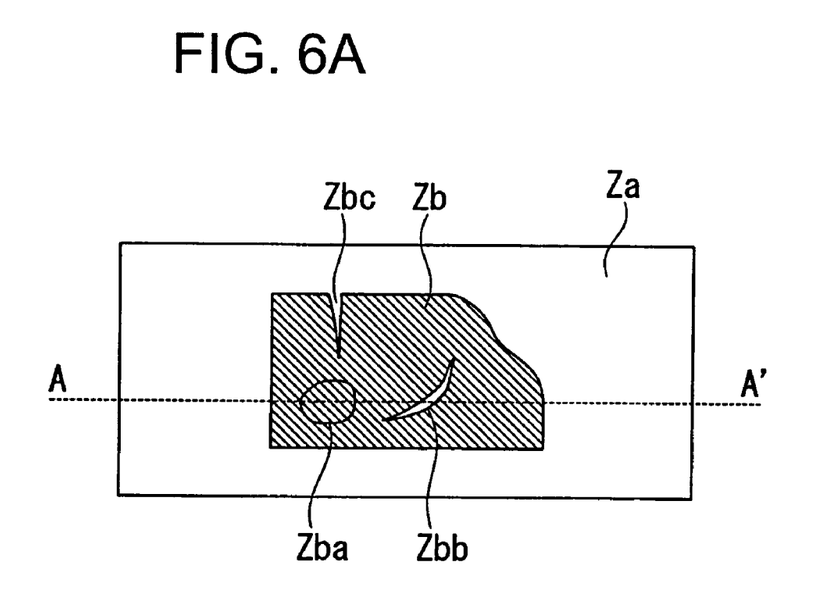
FIG. 6A and FIG. 6B are diagrams for explaining a processing method of an evaluation means in the automatic slicing apparatus of the embodiment of the present invention.
Figure 6B:
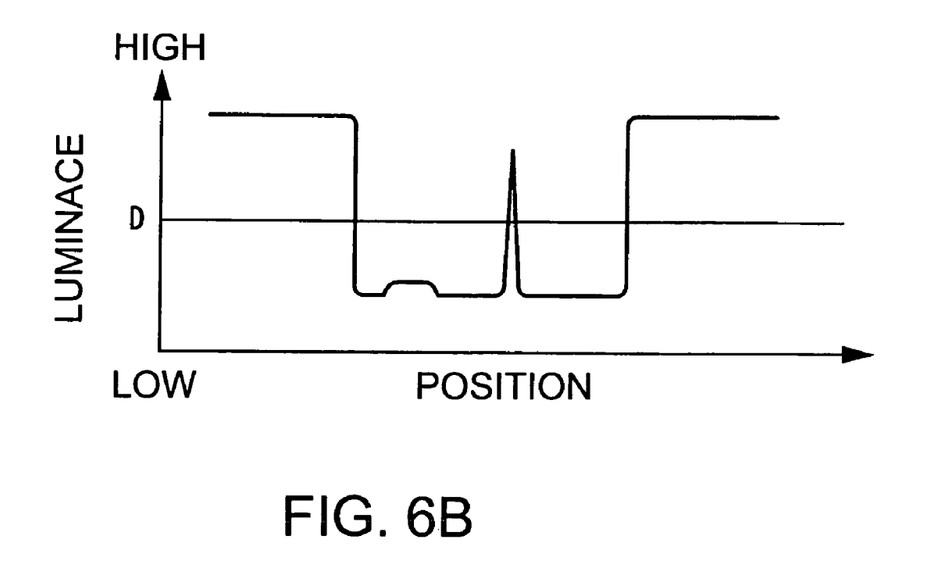
Figure 7:
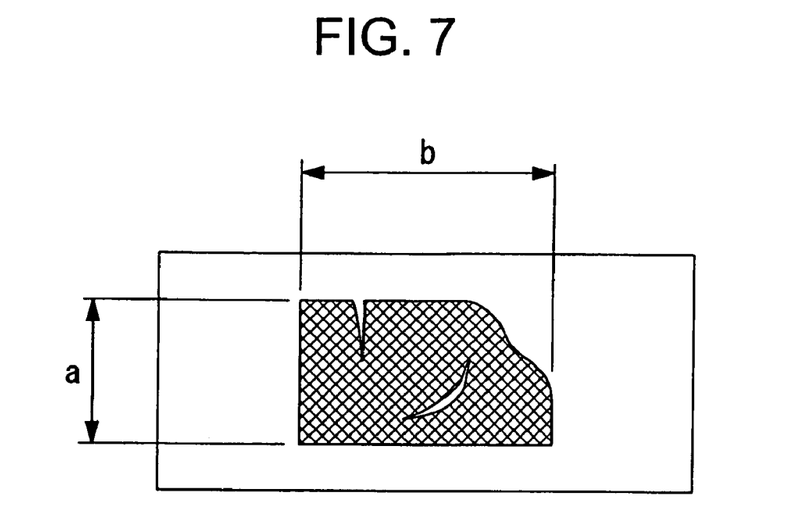
FIG. 7 is a diagram for explaining the processing method of the evaluation means in the automatic slicing apparatus of the embodiment of the present invention.

That is, such a luminance information as shown in FIG. 6B is obtained, e.g., from a portion along a line A-A' in a picture shown in FIG. 6A and, with respect to this luminance information, the binarization-processing is performed such that, with a previously set threshold value D being made a reference, a portion whose luminance is higher than the D becomes white, and a portion whose luminance is lower than the D becomes black. A picture having been obtained by this processing is shown in FIG. 7. The light-dark data of this picture and the sample block cut face data having been previously inputted are compared with at least one element among an area element, a position element of barycenter, and a pattern matching element.

By this, it is possible to judge whether or not there is a defect of the sliced piece 6, e.g., an external shape abnormality due to a wrinkle and a notch of the sliced piece 6, a break of the sliced piece, and an omission of the organism sample from the paraffin portion.

For example, when comparing by the area element, an area (area (a×b)) of the sliced piece) indicated by black in the light-dark data shown in FIG. 7 and a previously inputted area of the sample block having been cut off are compared and, if the area (area of the sliced piece) indicated by black is, e.g., 95% or more of the area of the sample block having been cut, there is judged "good" and, in a case where it is less than 95%, there is judged "not good".

Further, when comparing by the position element of barycenter, there is judged how much degree a barycenter position of a portion indicated by black in FIG. 7 deviates from a barycenter position of a cut-off portion of the sample block and, if its deviation amount is below a certain value, there is judged "good" and, if the deviation amount exceeds the certain amount, there is judged "not good".

Further, when comparing by the pattern matching element, the picture is partitioned in a certain size and, in the respective partitioned portions, there is judged whether images coincide. And, there is judged how much degree with respect to the whole there exist portions where the images don't coincide and, if its rate is below a certain value, there is judged "good" and, if the rate exceeds the certain value, there is judged "not good".

As to the three judgment elements having been mentioned above, among them there may be adopted one, two or all three. For example, in a case where the three are adopted, if the two among the three judgment elements are "good", there may be resultantly judged "good" and, in a case where the three judgment elements are all "not good" or only one judgment element is "good" and the other two are "not good", there may be resultantly judged "not good", so that their combination is arbitrary.

Incidentally, since the judgment on whether the sliced piece 6 having been cut like this is good or not good is performed mainly by the luminance information among the picture data, as a light source of the epi-illumination system 14, there is rather desired one emitting a blue system light in which a scattering phenomenon remarkably appears and whose wavelength is short.

In a case where there has been judged "good" by the evaluation means, subsequently there shifts to a step S7, and there is judged whether there exists the sample block which must be subsequently processed and, in a case where there exists the sample block which must be processed, there is transmitted the exchange command signal to the effect that the sample block 3 is exchanged from the evaluation means 16 to the sample block attaching/detaching means 4. Whereupon, in the sample block attaching/detaching means 4, the sample block existing at present is detached (step S8), and instead a new sample block is set onto the cutting base 2 (step S1). Hereafter, the steps S2-S6 are repeated. On the other hand, in a case where in the step S7 there has been judged that there exists no sample block which must be processed, the processing ends.

Further, in the step S6, in a case where the judgment by the evaluation means 16 is "not good", one is counted, and there is judged whether or not a count number has reached to a predetermined value (steps S9, S10). That is, this count number is a number denoting how many times the main cutting has been performed. In a case where the count number has not reached to the predetermined value, there shifts to the step S3, and the main cutting is performed again. On the other hand, in a case where the count number has reached to the predetermined value, it is deemed that no cutting margin exists already in the sample block 3, and there ends after transmitting an output signal of an error indication (step S11). Incidentally, in a point of time at which the rough cutting has finished, a value of n denoting the number of times of the main cutting is reset to "0".

Incidentally, thereafter in compliance with a necessity, the sliced piece 6 having floated on the water tank 9 is scooped up by a stained glass and, thereafter, the sliced piece specimen is made through a hot water extension process and a drying process.

If it is the automatic slicing method like this, since the sample block 3 is exchanged only in the case where there has been judged "good" by the evaluation means 16 and the sliced piece 6 is cut again from the same sample block 3 in the case "not good", the fear of failing to make the sliced piece specimen is extremely small even if continuously operated.

Further, it is possible to continuously cut the sliced piece 6 from the plural sample blocks 3 having been previously stored in the block keeping storehouse 11.

Incidentally, the present invention is not limited to the above-mentioned embodiment, and various modifications in design are possible in a scope not deviating from a gist of the invention.

For example, in the embodiment, as to the sliced piece 6 having been obtained, in order to perform the judgment on "good" or "not good" by the evaluation means 16, although there is performed with the sliced piece 6 having floated in the water tank 9, i.e., one after the water extension, being made an object, there is not limited to this, and there may be judged with the sliced piece 6 just after the cutting, or after the hot water extension and after the extension having used a hot plate being made the object.

Figure 8:
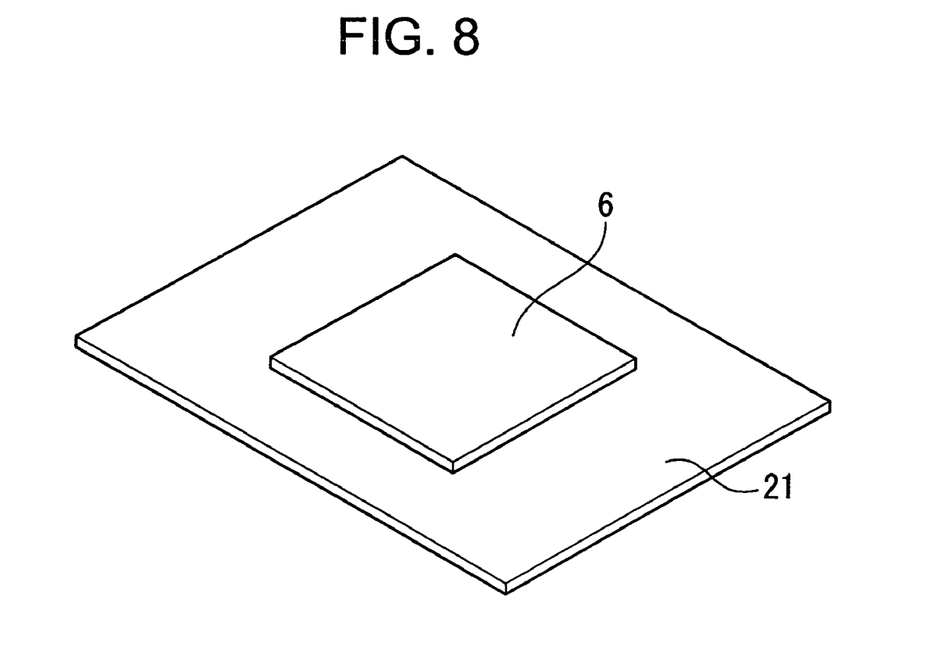
FIG. 8 is a perspective view showing an example of an observation method of the sliced piece by the observation means of the embodiment of the present invention.
Figure 9:
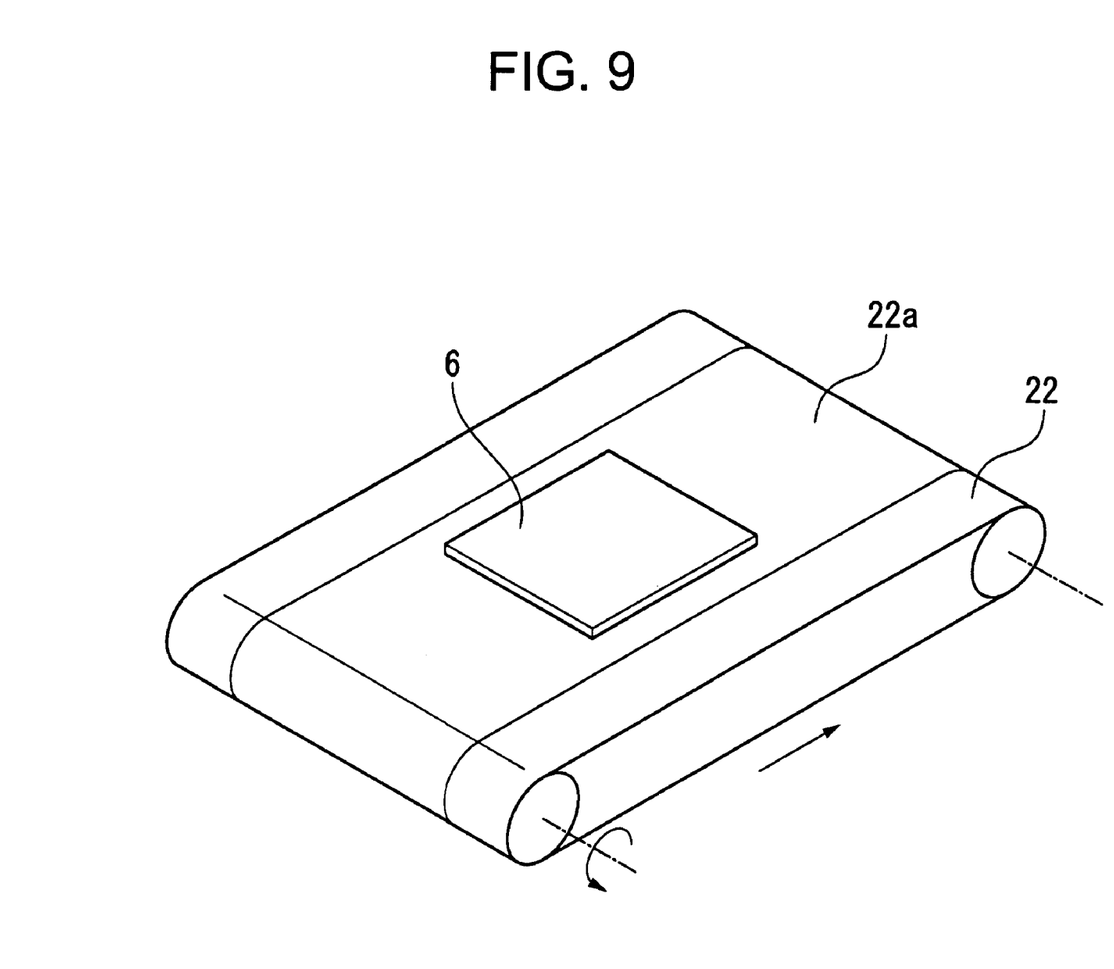
FIG. 9 is a perspective view showing other example of the observation method of the sliced piece by the observation means of the embodiment of the present invention.

Further, in the embodiment, for the observation, although the water having been stored in the water tank 9 is utilized as the mirror-reflecting medium on which the sliced piece 6 is mounted, there is not limited to this, and there may be utilized such a slide glass 21 as shown in FIG. 8, or there may be utilized, e.g., such a belt 22 having a mounting part 22*a* made of a metal foil having been mirror-finished as shown in FIG. 9.

Further, in the embodiment, in the evaluation means 16, in order to compare with the observation data having been obtained by the observation means, although the sample block cut face data having been previously inputted by the hand is made the reference, there is not limited to this, and there may be taken the image of the sample block having been cut by an image pickup means 23, such as CCD, as shown by alternate long and short dashed lines in FIG. 1 and the picture data of an external shape of the sample block 3, which has been taken in from the image, may be utilized as the reference.

Further, in the embodiment, although there is judged whether the sliced piece 6 is good or not good by the evaluation means 16 by comparing the observation data having been obtained by the observation means 10 and the sample block cut face data having been previously inputted, there is not limited to this, and there may be judged whether the sliced piece 6 is good or not good only by the observation data having been obtained by the observation means 10. In that case, the judgment on whether it is good or not good is performed with whether an external shape of the sliced piece 6 becomes a straight line or a curved line, whether or not there exists inside the sliced piece 6 a hole in which the organism sample has been omitted, or the like being made the reference.

Of course, also when judging whether the sliced piece 6 is good or not good only by the observation data having been obtained by the observation means 10, there may be judged on the basis of the light-dark data having been obtained by binarization-processing the observation data.

Figure 10:
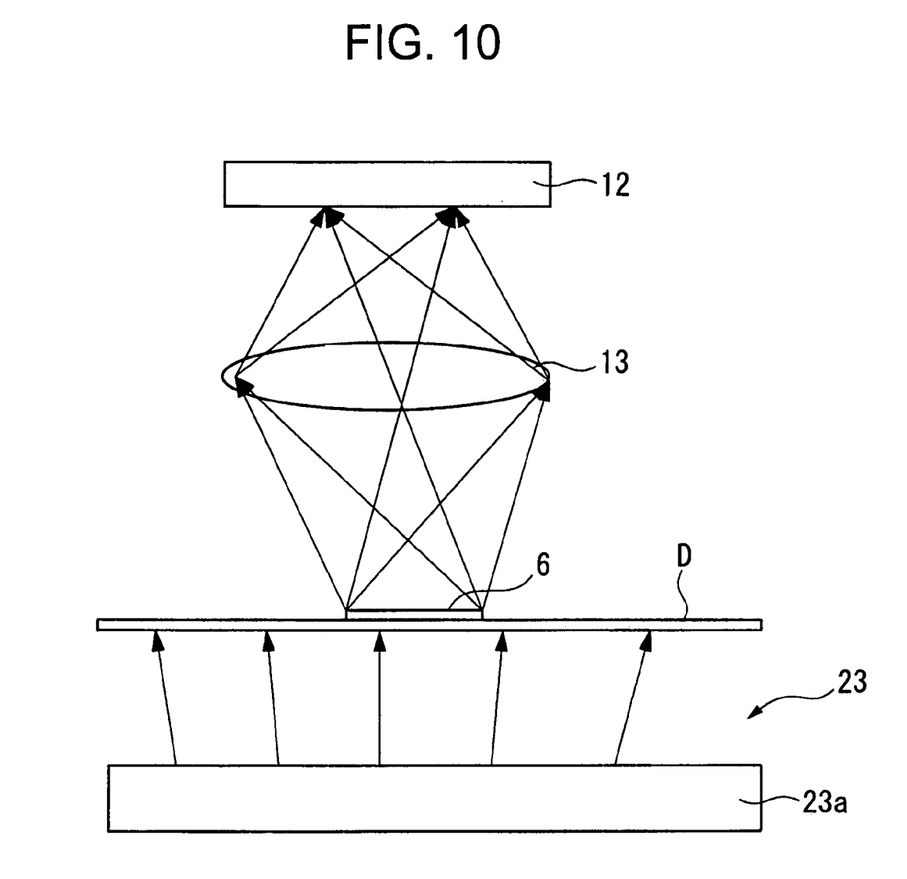
FIG. 10 is a side view showing still other example of the observation method of the sliced piece by the observation means of the embodiment of the present invention.

Further, in the embodiment, in order to obtain the observation data for judging whether the sliced piece is good or not good, although the image of the sliced piece having been disposed on the surface of the mirror-reflecting medium is obtained by taking it together with the peripheral medium by utilizing the light having been irradiated by the epi-illumination system 14, there is not limited to this, and as shown in FIG. 10, the image of the sliced piece 6 having been disposed in an inside or on a surface of a transparent medium (e.g., the slide glass, a transparent tape and the like correspond) D may be obtained by taking it together with the peripheral transparent medium D by utilizing the light having been irradiated by a transmission illumination system 24. Incidentally, as a light source 24*a* of the transmission illumination system 24, there suffices if it is a constitution capable of uniformly illuminating the object article to be irradiated such as a face light emitting element for instance, and there is not necessary required to be the parallel light. Further, in a case where there is irradiated by the transmission illumination system 24, when the sliced piece 6 is thin in some extent, there is a fear that a detection becomes difficult because the light permeates the sliced piece 6 itself. In that case, it can be coped with by increasing a resolving power of luminance of the image pickup element 12 to about 10-16 bits for instance.

What is claimed is:

1. An automatic slicing apparatus comprising:
   a sample block attaching/detaching device which, on the basis of an exchange command signal, detaches a sample block attached to a cutting base and attaches a new sample block to the cutting base;
   a cutting device which cuts a sliced piece of a predetermined thickness by relatively moving a knife with respect to the sample block having been attached to the cutting base;
   an observation device observing the sliced piece having been cut;
   an evaluation device which judges whether the sliced piece is good or not good by an observation data having been obtained by the observation device and which, when there has been judged that the sliced piece is good, transmits an exchange command signal to the effect that the sample block is to be exchanged to the sample block attaching/detaching device;
   a water tank that extends the sliced piece having been cut; and
   a carrier device carrying the sliced piece having been cut such that the sliced piece having been cut is immersed in the water tank,
   wherein the observation data is a picture data obtained clearly by taking by an epi-illumination system applying a collimate light parallel to a normal of a surface of a mirror-reflecting liquid medium in the water tank, when the sliced piece has been extended, an image of the sliced piece having been disposed on a surface of a mirror-reflecting liquid medium in the water tank, together with the liquid medium around the sliced piece.

2. An automatic slicing apparatus according to claim 1, wherein the evaluation device judges whether the sliced piece is good or not good by a light-dark data having been obtained by binarization-processing the picture data on the basis of a luminance information.

3. An automatic slicing apparatus according to claim 1, wherein the evaluation device judges whether the sliced piece is good or not good by comparing the observation data having been obtained by the observation device and a sample block cut face data having been previously inputted and, when there has been judged that the sliced piece is good, transmits the exchange command signal to the effect that the sample block is to be exchanged to the sample block attaching/detaching device.

4. An automatic slicing apparatus according to claim 3, wherein the evaluation device judges whether the sliced piece is good or not good by comparing a light-dark data having been obtained by binarization-processing the picture data on the basis of a luminance information and the sample block cut face data.

5. An automatic slicing apparatus according to claim 4, wherein, in the evaluation device, when comparing the light-dark data and the sample block cut face data, a virtual sliced piece picture obtained from the light-dark data and a sample block cut face picture obtained from the sample block cut face data are compared with at least one element among an area element, a position element of barycenter, and a pattern matching element.

6. An automatic slicing apparatus according to claim 1, wherein the epi-illumination system comprises a face light emission source making a collimate light, and a half mirror which reflects the collimate light having been irradiated from the face light emission source to the sliced pieced side, and through which the reflected light from the sliced piece permeates with a peripheral medium.

* * * * *